US012279891B2

(12) United States Patent
Babu et al.

(10) Patent No.: US 12,279,891 B2
(45) Date of Patent: Apr. 22, 2025

(54) PHONOCARDIOGRAM (PCG)-BASED IN-CABIN HEART MONITORING

(71) Applicant: Analog Devices International Unlimited Company, Limerick (IE)

(72) Inventors: Sudheer Babu, Therlam mandal (IN); Harsh Bolia, Udaipur (IN)

(73) Assignee: ANALOG DEVICES INTERNATIONAL UNLIMITED COMPANY, Limerick (IE)

( * ) Notice: Subject to any disclaimer, the term of this patent is extended or adjusted under 35 U.S.C. 154(b) by 406 days.

(21) Appl. No.: 17/691,551

(22) Filed: Mar. 10, 2022

(65) Prior Publication Data
US 2022/0338814 A1 Oct. 27, 2022

(30) Foreign Application Priority Data
Apr. 22, 2021 (IN) .............................. 202141018648

(51) Int. Cl.
*A61B 5/00* (2006.01)
*A61B 5/024* (2006.01)

(52) U.S. Cl.
CPC .......... *A61B 5/6893* (2013.01); *A61B 5/0004* (2013.01); *A61B 5/0024* (2013.01); *A61B 5/024* (2013.01); *A61B 5/7214* (2013.01); *A61B 5/746* (2013.01)

(58) Field of Classification Search
CPC ... A61B 5/6893; A61B 5/0004; A61B 5/0024; A61B 5/024; A61B 5/7214; A61B 5/746
See application file for complete search history.

(56) References Cited

U.S. PATENT DOCUMENTS

| 10,034,631 | B1 * | 7/2018 | Gallagher | B60N 2/0035 |
| 2004/0111045 | A1 * | 6/2004 | Sullivan | A61B 5/6892 600/595 |
| 2016/0100803 | A1 * | 4/2016 | Korzinov | A61B 5/389 600/301 |
| 2017/0209053 | A1 * | 7/2017 | Pantelopoulos | A61B 5/7264 |
| 2020/0121215 | A1 * | 4/2020 | Hyde | G01S 7/40 |

OTHER PUBLICATIONS

Leonhardt et al., *Unobtrusive Vital Sign Monitoring in Automotive Environments—A Review*, Sensors 2018, 18, 3080, MDPI, 38 pages.
Sidikova et al., *Vital Sign Monitoring in Car Seats Based on Electrocardiography, Ballistocardiography and Seismocardiography: A Review*, Sensors 2020, 20, 5699, MDPI, 28 pages.

* cited by examiner

*Primary Examiner* — Paula J Stice
(74) *Attorney, Agent, or Firm* — ARENTFOX SCHIFF LLP

(57) ABSTRACT

A heart monitoring system includes at least two sensors embedded in a seat, such as a driver's seat in a vehicle. One of the sensors obtains a phonocardiogram (PCG) of the driver's heart in addition to noise. Another sensor is a reference sensor that obtains a noise signal, but does not include the PCG signal. Processing circuitry receives the heart signal with the noise and the reference noise signal, and performs adaptive filtering to remove the noise from the heart signal. Further analysis detects a heart rate or other heart measurements in the heart signal, and may output an alert if a heart condition is detected.

20 Claims, 6 Drawing Sheets

PHONOCARDIOGRAM (PCG)-BASED IN-CABIN HEART MONITORING

PRIORITY DATA

This application claims priority to Indian provisional patent application no. 202141018648, filed Apr. 22, 2021, entitled "PHONOCARDIOGRAM (PCG)-BASED IN-CABIN VITAL SIGNS MONITORING," which is hereby incorporated by reference in its entirety.

TECHNICAL FIELD OF THE DISCLOSURE

The present invention relates to the field of vital sign monitoring, in particular to in-vehicle heart monitoring using acoustic sensors.

BACKGROUND

Vital sign monitoring of vehicle drivers can be used to determine whether a driver is alert and is not experiencing any medical issues that compromise the driver's ability to drive. For example, an abnormally elevated or depressed heart rate may indicate a medical condition that is unsafe for driving. Ensuring that only healthy and alert drivers are driving can improve roadway safety and reduce accident rates.

Existing driver monitoring systems include sensors that monitor behavior, such as eye tracking sensors and head movement sensors. These sensors do not directly monitor vital signs, and may result in delayed detection of impairment. Direct vital sign monitoring systems include electrocardiograph (ECG) electrodes mounted on a steering wheel or on wearable devices. These systems are inconvenient for drivers and may lead to compliance issues, e.g., if a driver does not wear a wearable device, or if the driver does not position his hands correctly on the ECG sensors on the steering wheel.

BRIEF DESCRIPTION OF THE DRAWINGS

To provide a more complete understanding of the present disclosure and features and advantages thereof, reference is made to the following description, taken in conjunction with the accompanying figures, wherein like reference numerals represent like parts, in which.

DESCRIPTION OF EXAMPLE EMBODIMENTS OF THE DISCLOSURE

Overview

Figure 1A:
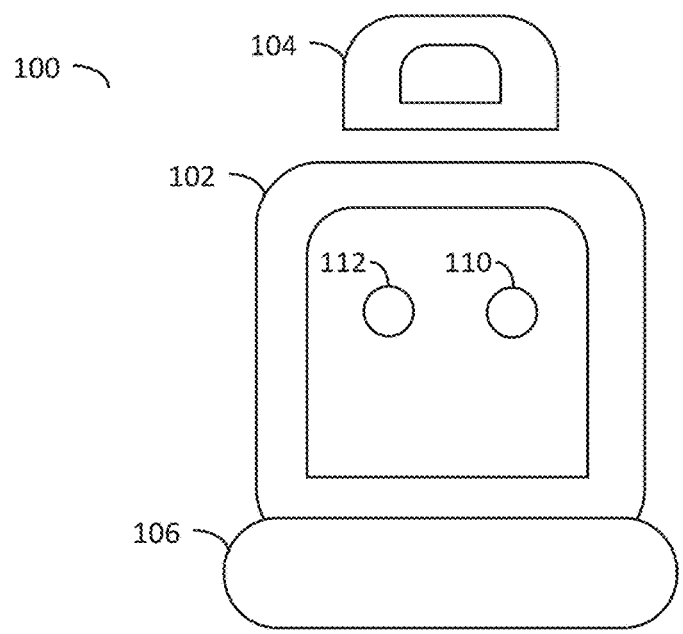
FIGS. 1A, 1B, and 1C illustrate three example car seats with sensors mounted in or on the backrests, according to some embodiments of the present disclosure.

The systems, methods and devices of this disclosure each have several innovative aspects, no single one of which is solely responsible for all of the desirable attributes disclosed herein. Details of one or more implementations of the subject matter described in this specification are set forth in the description below and the accompanying drawings.

A phonocardiogram (PCG) is an acoustic signal associated with heart activity. Acoustic sensors, such as microphones or piezoelectric sensors, can be positioned on or near a person's body to capture sounds of the person's heart. For example, a digital stethoscope may be used to capture heart sounds; the digital stethoscope may amplify sounds or sounds in a particular frequency range that includes heart sounds, and convert the captured sounds to a digital format for further processing.

Multiple sensors are positioned around a seat, such as a driver's seat in an automobile, to capture heart sounds of a person sitting in the seat. For example, a sensor is placed in the backrest of a driver's seat proximate to the driver's heart. The sensor may be positioned on the left side of the backrest, at a height along the backrest that is near an average driver's heart. In some embodiments, multiple sensors may be placed at different heights along the backrest to accommodate hearts at different vertical positions (e.g., drivers of different heights). For example, multiple sensors (e.g., two, three, four, or more) may be positioned along a vertical line along a left side of the backrest of the driver's seat. Furthermore, multiple sensors may be placed at different horizontal positions along the backrest to accommodate hearts at different horizontal positions (e.g., drivers of different widths). For example, a grid of four, six, eight, nine, or a different number of sensors may positioned across the left side of the backrest of the driver's seat. As another example, since heart positions generally move farther away from a center line of a human's body with increased height, multiple sensors may be positioned along a diagonal or curved line that moves away from a center line of the backrest as the acoustic sensors move up the backrest.

In an automobile setting, the sensors capture sound from various noise sources in addition to the driver's heart sounds. Noise sources include engine noise, speech from the driver and/or passengers, in-car audio sources (e.g., music, navigation instructions), body movements of the driver, and breathing. External noises may also travel into the vehicle and be detected by the sensors, such as other cars' engine sounds, speakers, horns, or sirens. To remove the effect of noise in the captured heart signal, one or more reference sensors are placed in the backrest of the driver's seat. A reference sensor may be placed along the right side of the backrest so that the reference sensor captures no heart sounds, or an attenuated heart sound compared to the sensor(s) on the left side of the backrest, but otherwise captures similar noises to the sensor(s) on the left side of the backrest. A signal from the reference sensor can be used to filter out the noise in the signal from the sensor(s) that captures the heart sounds. In some embodiments, multiple reference sensors may be included.

Each of the sensors captures a respective signal (e.g., an audio recording) and transfers the captured signal to processing circuitry. A signal from a sensor on the left side of the backrest that capture the heart sounds is referred to as a target signal, while the signal from the reference sensor is referred to as a reference signal. The processing circuitry uses the reference signal to filter the noise contribution from the target signal, e.g., using an adaptive filtering algorithm. The processing circuitry further one or more heart measurements, such as heart rate, based on the filtered signal. The heart measurements may characterize the driver's heart rhythm and can be used to identify a health event in the driver. In some embodiments, the processing circuitry computes heart measurements for certain time intervals, or selects to use heart measurements from certain time intervals. For example, the processing circuitry may discard data or heart measurements for intervals in which the user is speaking, or if the processing circuitry determines that noise that cannot be adequately filtered is present.

The processing circuitry may compare the determined heart rate to one or more thresholds to determine a state of the driver. For example, the processing circuitry may compare the heart rate to one or more earlier heart rates to determine if the driver as experienced a sudden change in heart rate. Alternatively, the processing circuitry may compare the heart rate to one or more absolute thresholds that may indicate a health event (e.g., whether the heart rate is lower than 40 beats per minute, or whether the heart rate is higher than 200 beats per minute). If the processing circuitry identifies that the driver has an irregular heart rhythm or heart rate, the processing circuitry may output an alert. The alert may be output to another vehicle component, e.g., to alert the driver, or to automatically stop or pull over the vehicle. In some embodiments, the alert is transmitted outside the vehicle, e.g., to a 9-1-1 center or to another emergency services provider.

The sensor system described herein may be used in other use cases besides driver monitoring. For example, a similar sensor system may capture and analyze heart sounds in any automobile seat, including passenger seats. As another example, the sensor system may be embedded in an infant car seat or other child safety seat, and the sensor system may output an alert (e.g., an audio alert) if the sensor system detects an abnormal change in the heart rate in the child safety seat. The sensor system described herein may also be used in other types of vehicles, such as airplanes, boats, trucks, recreational vehicles (RVs), etc., and/or in non-vehicle applications.

Embodiments of the present disclosure provide a system for monitoring a heart condition, where the system includes a first sensor, a second sensor, and processing circuitry. The first sensor positioned is in a backrest of a vehicle seat, and the first sensor is positioned along a left side of the backrest to capture a target signal comprising heart sounds and noise. The second sensor is positioned in the backrest of the vehicle seat, and the second sensor is positioned along a right side of the backrest to capture a reference signal. The processing circuitry is to receive the target signal and the reference signal; filter the target signal using the reference signal to generate a filtered signal, where filtering the target signal removes at least a portion of the noise from the target signal; and determine a heart measurement based on the filtered signal.

Further embodiments of the present disclosure provide a method for monitoring a heart rhythm, and a non-transitory computer-readable media having instructions stored thereon, where the instructions, when executed by a device, cause the device to perform the method. The method includes obtaining a target signal from a first sensor positioned in a backrest of a vehicle seat, the first sensor positioned along a left side of the backrest to capture a heart sounds and noise; obtaining a reference signal from a second sensor positioned in the backrest of the vehicle seat, the second sensor positioned along a right side of the backrest; filtering the target signal using the reference signal to generate a filtered signal, where filtering the target signal removes at least a portion of the noise from the target signal; and determining a heart measurement based on the filtered signal.

As will be appreciated by one skilled in the art, aspects of the present disclosure, in particular aspects of a PCG-based heart monitoring system, described herein, may be embodied in various manners (e.g., as a method, a system, a computer program product, or a computer-readable storage medium). Accordingly, aspects of the present disclosure may take the form of a hardware embodiment, a software embodiment (including firmware, resident software, microcode, etc.), or an embodiment combining software and hardware aspects that may all generally be referred to herein as a "circuit," "module" or "system." Functions described in this disclosure may be implemented as an algorithm executed by one or more hardware processing units, e.g. one or more microprocessors, of one or more computers. In various embodiments, different steps and portions of the steps of each of the methods described herein may be performed by different processing units. Furthermore, aspects of the present disclosure may take the form of a computer program product embodied in one or more computer-readable medium(s), preferably non-transitory, having computer-readable program code embodied, e.g., stored, thereon. In various embodiments, such a computer program may, for example, be downloaded (updated) to the existing devices and systems (e.g. to the existing perception system devices and/or their controllers, etc.) or be stored upon manufacturing of these devices and systems.

The following detailed description presents various descriptions of specific certain embodiments. However, the innovations described herein can be embodied in a multitude of different ways, for example, as defined and covered by the claims and/or select examples. In the following description, reference is made to the drawings where like reference numerals can indicate identical or functionally similar elements. It will be understood that elements illustrated in the drawings are not necessarily drawn to scale. Moreover, it will be understood that certain embodiments can include more elements than illustrated in a drawing and/or a subset of the elements illustrated in a drawing. Further, some embodiments can incorporate any suitable combination of features from two or more drawings.

The following disclosure describes various illustrative embodiments and examples for implementing the features and functionality of the present disclosure. While particular components, arrangements, and/or features are described below in connection with various example embodiments, these are merely examples used to simplify the present disclosure and are not intended to be limiting. It will of course be appreciated that in the development of any actual embodiment, numerous implementation-specific decisions must be made to achieve the developer's specific goals, including compliance with system, business, and/or legal constraints, which may vary from one implementation to another. Moreover, it will be appreciated that, while such a development effort might be complex and time-consuming; it would nevertheless be a routine undertaking for those of ordinary skill in the art having the benefit of this disclosure.

In the Specification, reference may be made to the spatial relationships between various components and to the spatial orientation of various aspects of components as depicted in the attached drawings. However, as will be recognized by those skilled in the art after a complete reading of the present disclosure, the devices, components, members, apparatuses, etc. described herein may be positioned in any desired orientation. Thus, the use of terms such as "above", "below", "upper", "lower", "top", "bottom", or other similar terms to describe a spatial relationship between various components or to describe the spatial orientation of aspects of such components, should be understood to describe a relative relationship between the components or a spatial orientation of aspects of such components, respectively, as the components described herein may be oriented in any desired direction. When used to describe a range of dimensions or other characteristics (e.g., time, pressure, temperature, length, width, etc.) of an element, operations, and/or conditions, the phrase "between X and Y" represents a range that includes X and Y.

Other features and advantages of the disclosure will be apparent from the following description and the claims.

Example Sensor Arrangements

Figure 1B:
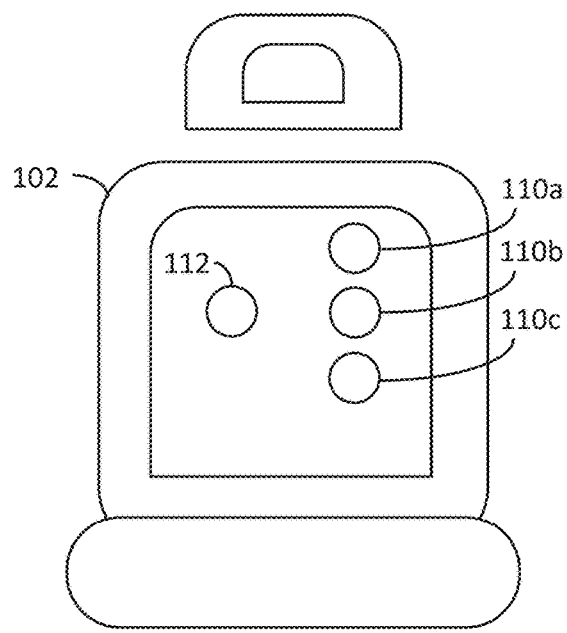
Figure 1C:
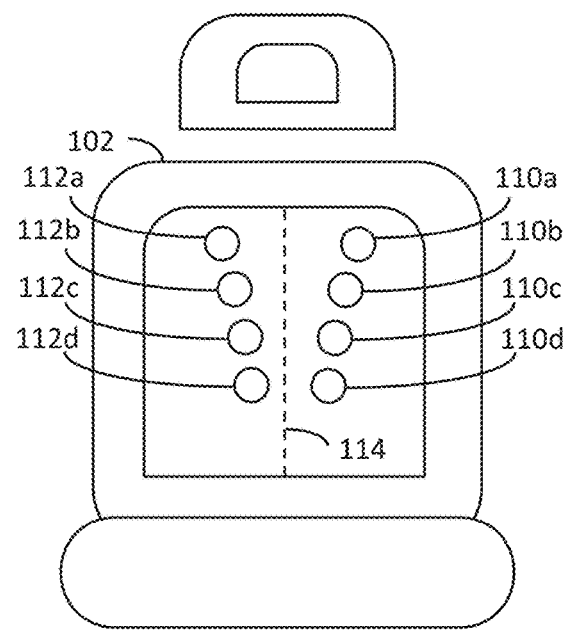

FIGS. 1A, 1B, and 1C illustrate three example car seats with sensors mounted in or on the backrests, according to some embodiments of the present disclosure. FIG. 1A illustrates a vehicle seat 100 having a backrest 102, a headrest 104, and a base 106. When a user sits in the vehicle seat 100, the user's back is positioned along the backrest 102, with the heart typically toward the left side of the backrest (corresponding to the right side in the view shown in FIG. 1A).

Two sensors 110 and 112 are positioned in the backrest 102. The sensors 110 and 112 may be digital stethoscopes, also referred to as electronic stethoscopes, that capture sound and convert the sound to an electrical signal. Digital stethoscopes may amplify captured sounds, or amplify sounds in a particular frequency range that includes heart sounds, and convert the amplified sounds to a digital format for further processing. A digital stethoscope may include an acoustic sensor (e.g., a microphone) to capture heart sounds. Alternatively, a digital stethoscope may include a piezoelectric sensor, which may use a piezoelectric crystal in combination with a diaphragm. Other types of sensors for capturing heart sounds, such as stethoscopes with electromagnetic diaphragms or Doppler stethoscopes, may alternatively be used.

Each of the sensors 110 and 112 captures a respective signal (e.g., an audio recording) and transfers the captured signal to processing circuitry. The sensor 110 is located on the left side of the backrest 102 from the orientation of a person sitting in the vehicle seat 100. The sensor 110 may be at a height along the backrest that is near an average driver's heart. The sensor 110 may be referred to as a heart sensor, as the sensor 110 is positioned near the heart of a person sitting in the vehicle seat 100. A signal captured by the sensor 110 is referred to as a target signal or heart signal. In some embodiments, to account for variability in heart positions of different drivers, multiple heart sensors 110 may be included, e.g., as shown in the example vehicle seats in FIGS. 1B and 1C.

A target signal captured by the sensor 110 typically includes noise. Noise sources include engine noise, speech from the driver and/or passengers, in-car audio sources (e.g., music, navigation instructions), body movements of the driver, and breathing. The vehicle seat 100 may include one or more additional reference sensors intended to capture the noise sources, but not capture heart sounds. Sensor 112 is an example of such a reference sensor.

The sensor 112 is located on the right side of the backrest 102 from the orientation of a person sitting in the vehicle seat 100. The sensor 112 is positioned away from the heart of a person sitting in the vehicle seat 100, but otherwise captures similar noise to the sensor 110. A signal captured by the sensor 112 is referred to as a reference signal. The reference signal can be used to filter the noise contribution from the target signal captured by the sensor 110.

The sensors 110 and 112 may be embedded in the backrest 102, e.g., underneath a fabric or leather seat cover. In this example, the sensors 110 and 112 may be hidden from view. Alternatively, the sensors 110 and 112 may exposed, e.g., extending through the seat cover, or fastened over top of the seat cover. Exposing the sensors 110 and 112 may improve sound capture, while embedding the sensors 110 and 112 under the seat cover protects the sensors and may improve their reliability and longevity.

As noted above, in some embodiments, multiple sensors may be placed at different heights along the backrest 102 to accommodate hearts at different vertical positions (e.g., drivers of different heights). FIG. 1B shows a first alternative embodiment with multiple heart sensors 110. In this example, multiple heart sensors 110a, 110b, and 110c are arranged in a vertical line along the left side of the backrest 102. While three sensors 110a, 110b, and 110c are shown in FIG. 1B, other numbers of sensors (e.g., two sensors 110, or four or more sensors 110) may be included in a vertical line.

In other embodiments, heart sensors 110 may also be positioned at multiple different horizontal positions along the backrest 102 to accommodate hearts at different horizontal positions. For example, a number of the sensors 110 (e.g., four, six, eight, nine, or a different number of the sensors 110) may positioned across the left side of the backrest 102 in a grid formation, e.g., a second vertical column of sensors 110 may be arranged next to the vertical column of sensors 110a, 110b, and 110c illustrated in FIG. 1B.

As another example, since heart positions generally move farther away from a center line of a human's body with increased height, multiple sensors 110 may be positioned along a diagonal or curved line that moves away from a center line of the backrest as the acoustic sensors move up the backrest. FIG. 1C illustrates four heart sensors 110a, 110b, 110c, and 110d that move outward from a center line 114 of the backrest 102.

In some embodiments with multiple heart sensors 110, e.g., the example shown in FIG. 1B, a single reference sensor 112 is included. In other embodiments with multiple heart sensors 110, e.g., the example shown in FIG. 1C, multiple reference sensors 112 are included. Four example reference sensors 112a, 112b, 112c, and 112d are shown in FIG. 1C. The reference sensors 112 and heart sensors 110 may be arranged symmetrically across a center line 114 of the backrest 102, as illustrated in FIG. 1C. In other embodiments, multiple reference sensors 112 may be included, but fewer reference sensors 112 than heart sensors 110.

If multiple reference sensors 112 are included, processing circuitry may select a reference signal from one of the reference sensors 112, e.g., the reference sensor 112 corresponding to a selected heart sensor 110 that captures the clearest heart sound in the target signal. For example, if the processing circuitry determines that the strongest heart signal is captured by the heart sensor 110c, the processing circuitry selects the reference sensor 112c to provide the reference signal used to filter noise from the heart signal. In some embodiments, if a driver has dextrocardia (a condition in which the heart is located on the right side of the body), one of the reference sensors 112 may be used to capture the heart signal, while one of the heart sensors 110 captures the reference signal. Including multiple reference sensors 112 can help ensure that a heart sound can be captured at more possible locations of a user's heart.

While FIGS. 1A-1C illustrate heart sensors 110 and reference sensors 112 in a vehicle seat, e.g., a driver's seat to detect a driver's heart rate, similar sensors may be included in other types of seats, and coupled to circuitry for detecting heart measurements for users sitting in such seats. For example, a sensor system may capture and analyze heart sounds in any automobile seat, including passenger seats. As another example, a sensor system may be included in an infant car seat or other child safety seat. If the child safety seat is intended for use for a range of child sizes (e.g., a particular age, weight, and/or height range), multiple heart sensors 110 and, in some cases, multiple reference sensors 112 may be included to adequately capture heart sounds across the range of child sizes for which the child safety seat is intended. The sensor system described herein may be particularly effective for a child safety seat, since a child is typically strapped into a five-point harness that permits minimal body motion. The sensor system in a child safety seat (or other type of seat) may output an alert (e.g., an audio alert) if the sensor system detects an abnormal change in the heart rate or other heart measurement. The sensor system may be used in other types of vehicles, such as airplanes, boats, trucks, RVs, etc. Furthermore, the sensor system may be used in non-vehicle applications, such as chairs used by patients in a healthcare setting, office chairs, etc.

Example Heart Monitoring System

Figure 2:
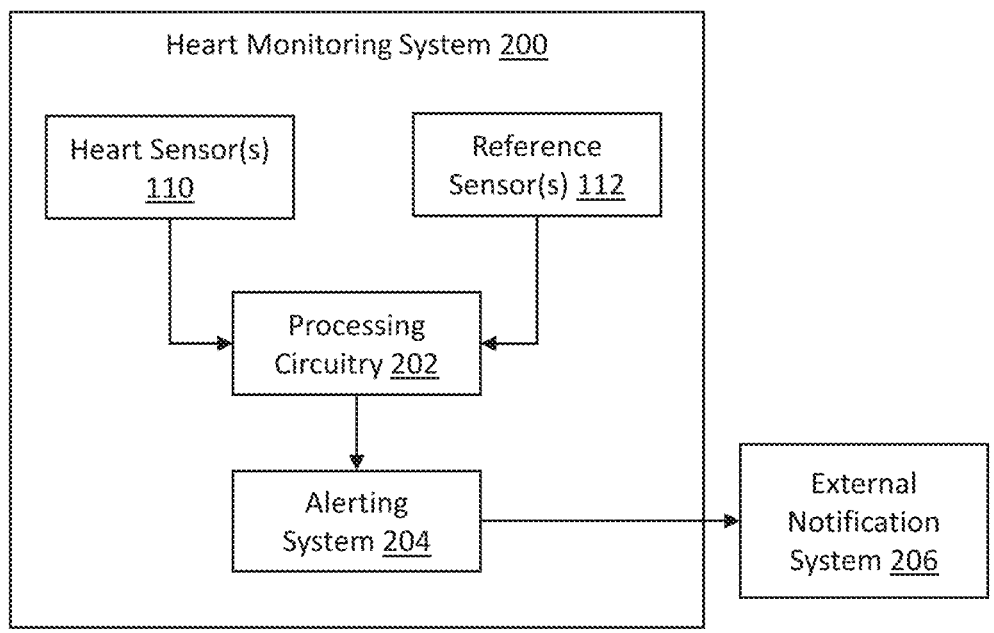
FIG. 2 is a block diagram of a heart monitoring system, according to some embodiments of the present disclosure.

FIG. 2 is a block diagram of a heart monitoring system, according to some embodiments of the present disclosure. The heart monitoring system 200 includes one or more heart sensors 110, one or more reference sensors 112, processing circuitry 202, and an alerting system 204. In this example, the alerting system 204 is in communication with an external notification system 206. In alternative configurations, different, fewer, and/or additional components may be included in the heart monitoring system 200 from those shown in FIG. 2. For example, the alerting system 204 may be included in the processing circuitry 202. The processing circuitry 202 may include one or more processing devices, which may be physically located inside or outside the vehicle. Furthermore, the functionality described in conjunction with one or more of the components shown in FIG. 2 may be distributed among the components in a different manner than described.

The heart sensor(s) 110 may be any of the heart sensors 110 described with respect to FIGS. 1A-1C. The reference sensor(s) 112 may be any of the reference sensors 112 described with respect to FIGS. 1A-1C. The heart sensor(s) 110 provide one or more target signals (or heart signals) to the processing circuitry 202. The reference sensor(s) 112 provide one or more reference signals to the processing circuitry 202. As noted above, a target signal includes a digital representation of heart sounds in addition to noise. The reference signal includes similar noise to the noise of the target signal. The reference signal does not include the heart sounds, or includes attenuated heart sounds, due to the reference sensor(s) 112 being located farther from a driver's heart than the heart sensor(s) 110.

The processing circuitry 202 receives the target signal(s) and the reference signal(s). If multiple target signals or multiple reference signals are received, the processing circuitry 202 may select one of or more of the target signals(s) and/or reference signal(s) for processing. For example, if the processing circuitry 202 receives or selects a single target signal and a corresponding reference signal, the processing circuitry 202 filters the target signal using the reference signal to generate a filtered signal. For example, the processing circuitry 202 uses an adaptive filtering algorithm, such as a recursive least squares (RLS) filter. Filtering the target signal removes at least a portion of the noise in the target signal from the target signal. The resulting filtered signal includes the heart sound component of the target signal. The resulting filtered signal may still include some noise. Typically, the filtered signal can be processed to determine one or more measurements of heart rhythm, such as a heart rate, heart rate variability (HRV), identification and/or measurements of S1 and S2 sounds, measurements of additional sounds (e.g., S3 and S4), or other types of heart rhythm measurements or heartbeat features that may be derived from a PCG signal.

The processing circuitry 202 may determine the state of the driver (or other person for whom heart measurements and reference measurements are taken) by applying one or more rules to the heart measurements. For example, the processing circuitry 202 may compare a determined heart rate and/or HRV to one or more thresholds. The processing circuitry 202 may, for example, compare the heart rate to one or more earlier heart rates to determine if the driver has experienced a sudden change in heart rate. As another example, the processing circuitry 202 may compare the heart rate to one or more absolute thresholds that may indicate a health event (e.g., whether the heart rate is lower than 40 beats per minute, or whether the heart rate is higher than 200 beats per minute). The processing circuitry 202 may learn a typical heart rate or heart rate range for a particular driver, and compare the measured heart rate to this range. As yet another example, the processing circuitry 202 may determine, based on HRV exceeding a certain threshold, or based on unexpected features (e.g., additional heart sounds) identified in the filtered signal, that a driver has an irregular heart rhythm.

If a health event is detected, the processing circuitry 202 may output a signal to the alerting system 204. The alerting system 204 may be coupled to one or more in-vehicle components for outputting an alert, such as a vehicle's speaker system or a vehicle's display. The alerting system 204 may output an alert for the driver to pull over and seek medical attention. In some embodiments, if the vehicle has a self-driving capability, the alerting system 204 may instruct the self-driving system to automatically pull over and stop the vehicle.

In some embodiments, the alerting system 204 is coupled to an external notification system 206, which may be coupled to a communications network (e.g., a cellular network or the Internet) to transmit requests or alerts. For example, the external notification system 206 may include a communications circuit in the vehicle that can request assistance, e.g., from a 9-1-1 center, or from another emergency services center (e.g., OnStar).

Example Process for Analyzing a Heart Signal

Figure 3:
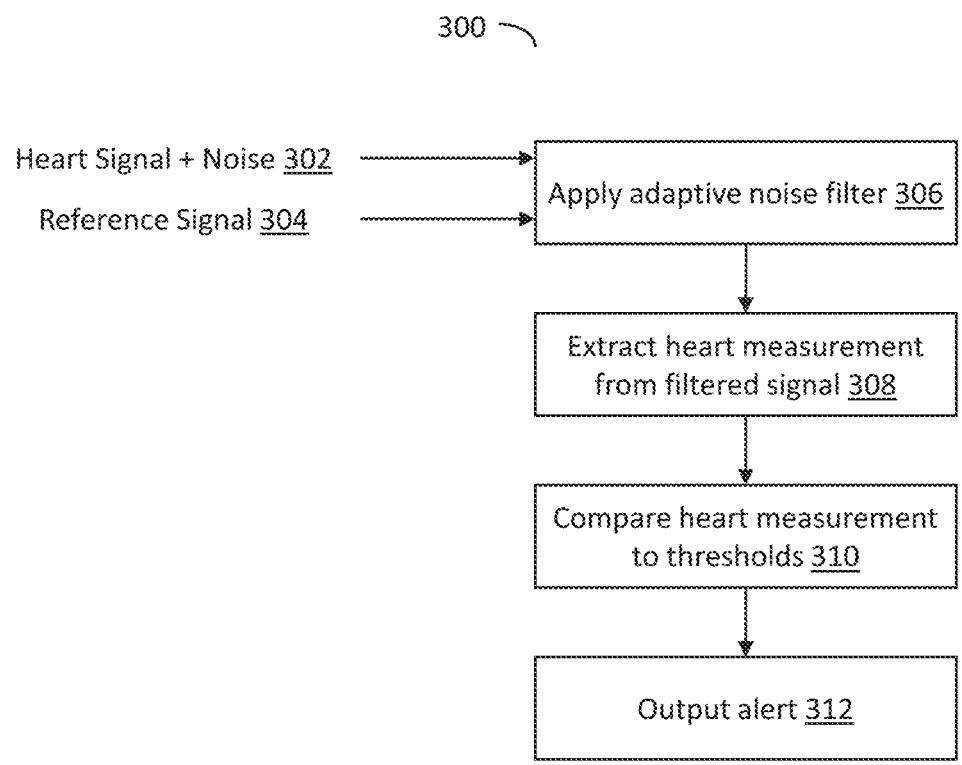
FIG. 3 is a flowchart of a process for analyzing a heart signal, according to some embodiments of the present disclosure.

FIG. 3 is a flowchart of a process 300 for analyzing a heart signal, according to some embodiments of the present disclosure. The process 300 may be performed by the heart monitoring system 200, and in particular, by the processing circuitry 202 described above.

The processing circuitry 202 receives a target signal, which includes a heart signal and noise 302, from a heart sensor 110. The processing circuitry 202 also receives a reference signal 304 from a reference sensor 112. The processing circuitry 202 applies 306 an adaptive noise filter to the heart signal and noise 302. The adaptive noise filter removes the noise component from the heart signal and noise 302 using the reference signal 304. The adaptive noise filter may be an RLS filter, as mentioned above. In other embodiments, other types of adaptive filters may be used, e.g., a least mean squares (LMS) filter, a tapped delay finite impulse response (FIR) filter, an adaptive linear combiner (ALC), a nonlinear adaptive filter, etc.

The processing circuitry 202 may perform additional processing steps before and/or after applying the noise filter. For example, the processing circuitry 202 may apply a band pass filter (e.g., a second order Butterworth band pass filter) to the target signal and/or the reference signal to select frequencies that include heart sounds (e.g., frequencies in the range of 10 Hz to 400 Hz). The processing circuitry 202 may perform various transforms or other data manipulations of the target signal, reference signal, and/or filtered signal, e.g., performing a Hilbert transformation of the target and reference signals, computing absolute value of signals, computing logarithms and/or exponentials, and/or applying additional filters (e.g., additional bandpass, lowpass, or high pass filters).

Having filtered the heart signal and noise 302 to generate the filtered signal, the processing circuitry 202 extracts 308 a heart measurement from the filtered signal. For example, the processing circuitry 202 calculates an envelope for the filtered signal and performs an autocorrelation of the envelope to detect the heart rate. In some embodiments, the processing circuitry 202 may further perform a fast Fourier transform (FFT) of the autocorrelation result and use the maximum value of the FFT as the heart rate. The processing circuitry 202 may continually or periodically perform autocorrelations of the processed signal to produce a heart rate signal over time. The processing circuitry 202 may further process the heart rate signal to determine the HRV.

The processing circuitry 202 compares 310 the heart measurement (e.g., the heart rate or HRV) to one or more thresholds to determine if the driver is experiencing a health event, e.g., an abnormally low heart rate, an abnormally high heart rate, or a high amount of HRV. More generally, the processing circuitry 202 may apply any of the thresholds or rules described with respect to FIG. 2. If the processing circuitry 202 determines that the heart measurement exceeds a high threshold or is lower than a low threshold, the processing circuitry 202 outputs 312 an alert signal to the alerting system 204, which may provide one or more internal (e.g., in-vehicle) or external alerts, as described with respect to FIG. 2.

Example Process for Filtering Known Noise from Target Signal

As described above, there may be several different sources of noise in a vehicle setting, such as engine noise, human speech, a stereo system, breathing, body movement, and external noises (e.g., other cars, sirens, etc.). In the case of a vehicle stereo, a digital representation of the output sound can be passed to the processing circuitry 202 and filtered from the target signal. Other known audio sources, such as sounds emitted from phones in the vehicle, may similarly be passed to the processing circuitry 202 for removal from the target signal if the digital representations of the sounds can be accessed by the vehicle or processing circuitry 202. Removing these noise components using the sound signal received from the stereo system or other noise source may be more effective than removing the noise components using the recording from the reference sensor 112.

Figure 4:
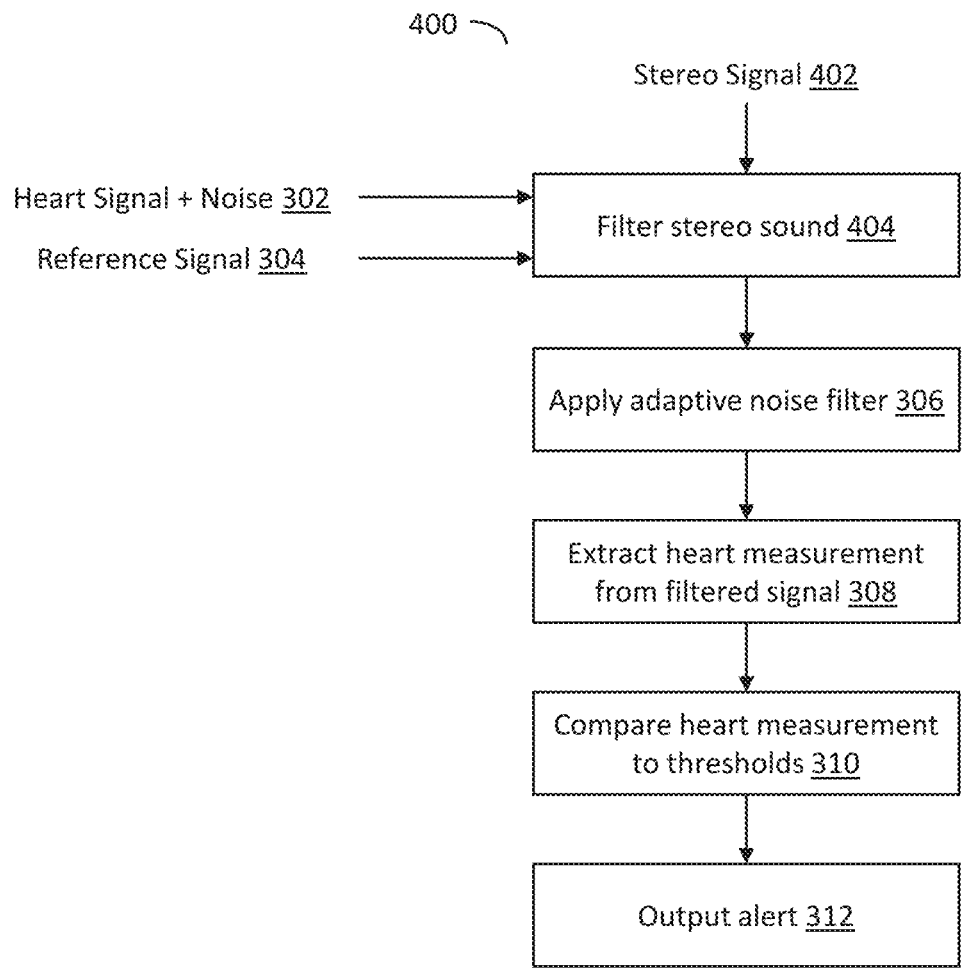
FIG. 4 is a flowchart of a process for analyzing a heart signal that includes filtering a known noise from the target signal, according to some embodiments of the present disclosure.

FIG. 4 is a flowchart of a process 400 for analyzing a heart signal that includes filtering a known noise from the target signal, according to some embodiments of the present disclosure. In this example, in addition to the heart signal and noise 302 (i.e., the target signal) and the reference signal 304, the processing circuitry 202 receives a stereo signal 402. The stereo signal 402 may be received directly from a stereo system, and is a digital representation of sound to be output, rather than a recording of sound that is actually output. The stereo signal 402 may be the same signal that a stereo system transmits to speakers in the vehicle. The stereo signal 402 may further include, or be modified by, output settings for the stereo system, e.g., volume, bass levels and/or treble levels, etc.

The processing circuitry 202 filters 404 the stereo signal 402 from the heart signal and noise 302. In some embodiments, the processing circuitry 202 also filters the stereo signal 402 from the reference signal 304, which also includes a noise component from the stereo system. Following the filtering the stereo sound, the process 400 proceeds with the processes 306-312 shown in FIG. 3 and described above.

Example Process for Selecting a Target Signal

Figure 5:
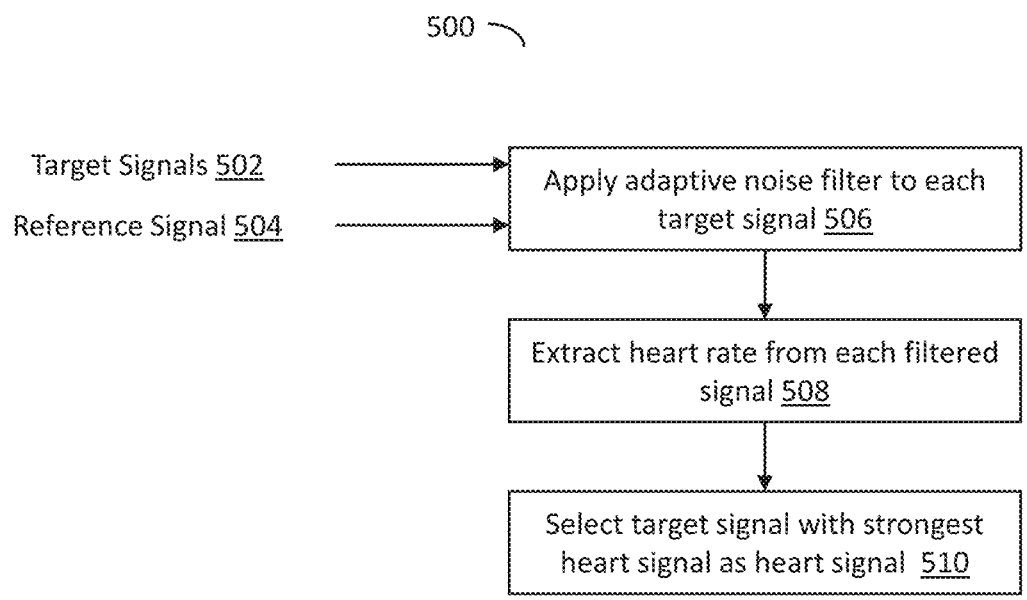
FIG. 5 is a flowchart of a process for selecting a target signal from a particular sensor, according to some embodiments of the present disclosure.

FIG. 5 is a flowchart of a process 500 for selecting a target signal from a particular sensor, according to some embodiments of the present disclosure. As described with respect to FIGS. 1B, 1C, and 2, in some embodiments, the heart monitoring system includes multiple heart sensors 110, and in some cases, multiple reference sensors 112. The processing circuitry 202 receives a set of target signals 502 and one or more reference signals 504 from the heart sensors 110 and reference sensor(s) 112. To select one of the target signals 502, in this example, the processing circuitry 202 applies 506 an adaptive noise filter to each target signal 502. The adaptive noise filter may be similar to the adaptive noise filter described with respect to FIG. 3. If multiple reference signals 504 are received, the processing circuitry 202 may pair a target signal 502 with a corresponding reference signal 504 based on their locations in the seat back. For example, referring to FIG. 1C, the processing circuitry 202 pairs the target signal from the heart sensor 110a with the reference signal from the reference sensor 112a, pairs the target signal from the heart sensor 110b with the reference signal from the reference sensor 112b, etc. If a single reference sensor 112 is included, the processing circuitry 202 uses the same reference signal 504 to filter each of the target signals 502.

The processing circuitry 202 extracts 508 a heart rate from each of the filtered signals. The processing circuitry 202 may extract the heart rates from the filtered signals as described above with respect to FIG. 3. The processing circuitry 202 then selects 510 the target signal 502 with the strongest or clearest heart signal as the heart signal for the driver. For example, the processing circuitry 202 may perform autocorrelation to extract the heart rate as described with respect to FIG. 3, and the processing circuitry 202 selects the target signal that provides the highest peak as the heart signal. As another example, the processing circuitry 202 selects the target signal having the most distinct heart rate peak (e.g., the autocorrelation result with the greatest difference between the highest peak and the second-highest peak, or the greatest ratio between the highest peak and the second-highest peak) as the heart signal. In some embodiments, the processing circuitry 202 may select a target signal based on other qualities of the filtered signals, without calculating the heart rate.

The processing circuitry 202 may use the selected target signal for analyzing the driver's heartbeat, calculating additional measurements, and/or providing alerts, as described with respect to FIG. 3. In some embodiments, the processing circuitry 202 may select multiple target signals, e.g., if two target signals have equally clear or strong heart signals.

Having selected a target signal, the processing circuitry 202 may use this target signal for ongoing analysis of the driver's heart, rather than continually repeating the process 500, as it may be assumed that the driver's heart does not change positions relative to the heart sensors 110. In some cases, the process 500 may be repeated on a periodic basis, e.g., once per minute. In some embodiments, the process 500 may be repeated if a health event is detected, to confirm that the strongest heart signal has not moved to a different heart sensor 110.

Example Process for Selecting Time Intervals of a Heart Signal

In some embodiments, even when the noise filtering described above is performed, the algorithm performed by the processing circuitry 202 may not be able to reliably detect a heartbeat in certain conditions. For example, if the driver is speaking, the sound of the driver's speech may corrupt the target signal to an extent that a reliable heart rate cannot be detected. In such conditions, the processing circuitry 202 may discard windows or intervals of data during which the heart signal is unreliable, while keeping other windows or intervals of data. In general, since a driver does not typically speak continuously without breaks, the heart monitoring system 200 may be able to adequately detect the driver's heart rate during non-speaking intervals and detect any heart-related problems during these intervals. Furthermore, if the driver is speaking, it may be assumed that the driver has not experienced a sudden medical event.

Figure 6:
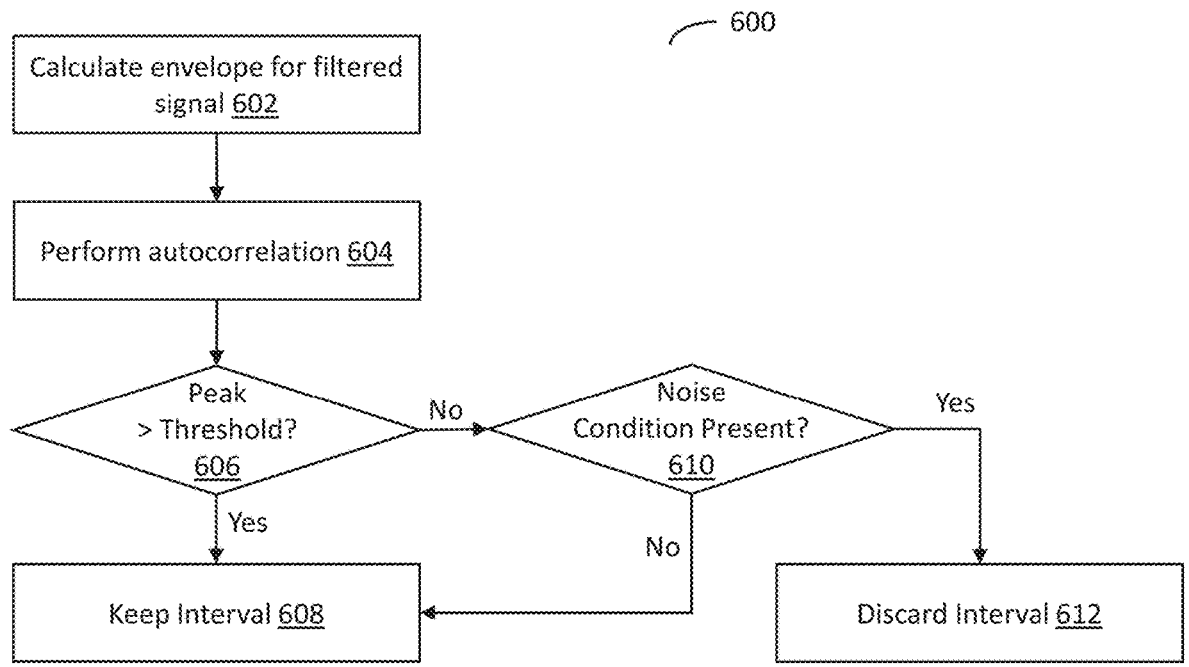
FIG. 6 is a flowchart of a process for selecting time intervals of a heart signal, according to some embodiments of the present disclosure.

FIG. 6 is a flowchart of a process 600 for selecting time intervals of a heart signal, according to some embodiments of the present disclosure. The processing circuitry 202 first filters a target signal to generate a filtered signal, e.g., as described with respect to FIG. 3 or FIG. 4. The processing circuitry 202 may further select a particular target signal, as described with respect to FIG. 5. Having filtered the target signal, the processing circuitry 202 calculates 602 a signal envelope for the filtered signal, e.g., using a Hilbert transform or a moving root mean square (RMS) amplitude. The envelope is a smooth curve that outlines the extremes of the filtered signal.

The processing circuitry 202 then performs 604 an autocorrelation of the envelope to find the heart rate in the filtered signal. Autocorrelation can be used to identify a repeating, periodic signal in a signal, e.g., to find a repeating heartbeat within a heart signal. If the noise has been adequately filtered from the heart signal, the peak of the autocorrelation represents the driver's heart rate. However, as noted above, in some situation, there may be too much residual noise to identify a heart rate from the autocorrelation.

The processing circuitry 202 determines 606 whether the autocorrelation has a peak that exceeds a threshold. For example, the processing circuitry 202 determines whether the peak of the autocorrelation exceeds a fixed threshold or exceeds a variable threshold that may be set based on previous autocorrelation results. In other examples, the processing circuitry 202 compares the peak to one or more additional peaks in the autocorrelation result to determine if the peak is sufficiently high or distinct.

If the autocorrelation peak exceeds a threshold or is sufficiently distinct, the processing circuitry 202 keeps 608 the time interval from which the autocorrelation was derived in a heart rate signal that characterizes the user's heart. If the autocorrelation peak does not exceed the threshold or is not sufficiently distinct, in some embodiments, the processing circuitry 202 performs additional processing of the target signal and/or reference signal to determine 610 whether a particular noise condition is present. For example, the processing circuitry 202 may analyze the target signal to determine whether the driver is speaking. For a time interval in which the noise condition is detected, the processing circuitry 202 may discard 612 the data for this time interval. If the noise condition is not detected, the processing circuitry 202 may keep the interval; without the noise condition, the data may indicate that the driver is experiencing a health event.

If the noise condition is present, the processing circuitry 202 may determine to resume heartbeat analysis when the noise condition has ended. Furthermore, the processing circuitry 202 may determine whether the driver is experiencing a health event using data from time intervals during which the noise condition is not present, e.g., an algorithm may select a window or set of windows during which the driver is not speaking for heart rate detection. In some embodiments, the selected window(s) may be of variable length based on noise conditions (e.g., if the driver stops speaking for 15 seconds, the processing circuitry 202 may determine a heart rate based on data from a window corresponding to those 15 seconds).

Figure 7:
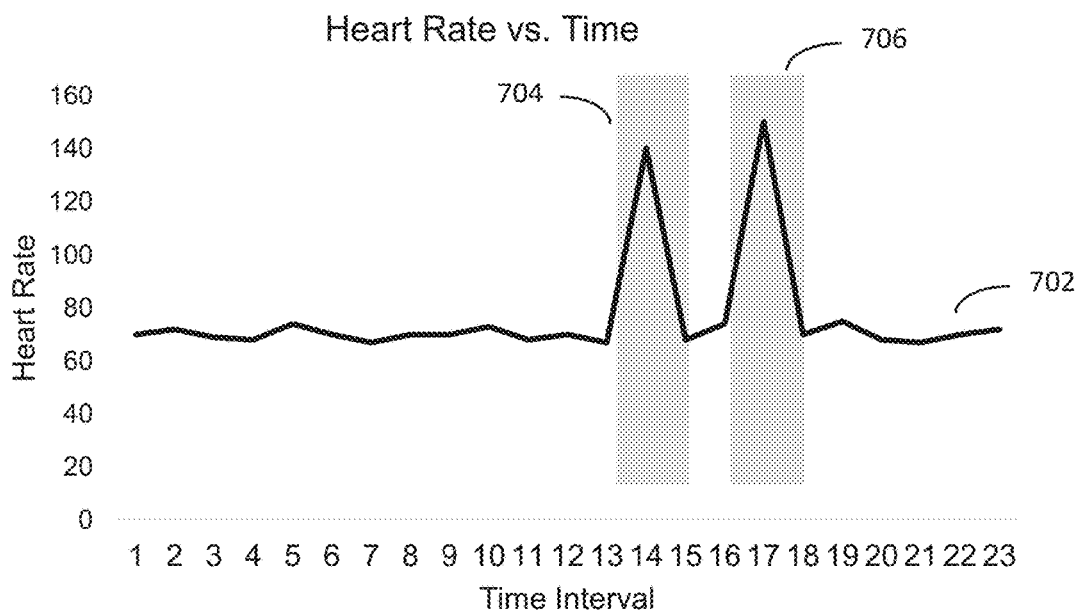
FIG. 7 is a chart showing example heart rate measurements obtained across multiple time intervals, according to some embodiments of the present disclosure.

FIG. 7 is a chart showing example heart rate measurements obtained across multiple time intervals, according to some embodiments of the present disclosure. The heart rate signal 702 indicates measured heart rates across a set of time intervals. The heart rate signal 702 has two time intervals 704 and 706 with abnormally high heart rates. If the processing circuitry 202 performing the process 600 determines that a noise condition (e.g., the driver speaking) is present during the time intervals 704 and 706, the processing circuitry 202 discards the data from the time intervals 704 and 706. The remaining time intervals do not indicate a health event, and thus the processing circuitry 202 can determine that the user is not experiencing a heart-related health event. By contrast, if the process 600 does not determine that a noise condition is present during the time intervals 704 and 706, the heart rates during these time intervals may indicate a health event, and the processing circuitry 202 may output an alert signal, as described with respect to FIG. 2.

Select Examples

Example 1 provides a system for monitoring a heart rhythm, the system including a first sensor positioned in a backrest of a vehicle seat, the first sensor positioned along a left side of the backrest to capture a target signal including heart sounds and noise; a second sensor positioned in the backrest of the vehicle seat, the second sensor positioned along a right side of the backrest to capture a reference signal; and processing circuitry to receive the target signal and the reference signal; filter the target signal using the reference signal to generate a filtered signal, where filtering the target signal removes at least a portion of the noise from the target signal; and determine a heart measurement based on the filtered signal.

Example 2 provides the system of example 1, where the heart measurement is a heart rate, and the processing circuitry is further to compare the heart rate to at least one threshold to determine whether a driver in the vehicle seat is experiencing a health issue.

Example 3 provides the system of example 1, where the heart measurement is heart rate variability (HRV), and the processing circuitry is further to determine whether a driver in the vehicle seat is experiencing a health issue at least in part based on the HRV.

Example 4 provides the system of example 1, where filtering the target signal includes performing an adaptive filtering algorithm.

Example 5 provides the system of example 4, where the adaptive filtering algorithm includes a recursive least squares (RLS) filter.

Example 6 provides the system of example 1, where the first sensor is one of an array of sensors at different positions along the left side of the backrest.

Example 7 provides the system of example 6, where the processing circuitry is to select the first sensor from the array of sensors along the left side of the backrest, the first sensor providing the strongest heart signal of the array of sensors.

Example 8 provides the system of example 6, where the processing circuitry is further to generate a plurality of filtered signals using the reference signal, each of the plurality of filtered signals based on a target signal from a respective one of the array of sensors; and determine the heart measurement based on the plurality of filtered signals.

Example 9 provides the system of example 1, where the first sensor is a first acoustic sensor, and the second sensor is a second acoustic sensor.

Example 10 provides the system of example 1, where the first sensor is a first piezoelectric sensor, and the second sensor is a second piezoelectric sensor.

Example 11 provides a method for monitoring a heart rhythm, the method including obtaining a target signal from a first sensor positioned in a backrest of a vehicle seat, the first sensor positioned along a left side of the backrest to capture a heart sounds and noise; obtaining a reference signal from a second sensor positioned in the backrest of the vehicle seat, the second sensor positioned along a right side of the backrest; filtering the target signal using the reference signal to generate a filtered signal, where filtering the target signal removes at least a portion of the noise from the target signal; and determining a heart measurement based on the filtered signal.

Example 12 provides the method of example 11, where the heart measurement is a heart rate, the method further including comparing the heart rate to at least one threshold to determine whether a driver in the vehicle seat is experiencing a health issue; and generating an alert in response to determining that the driver is experiencing a health issue.

Example 13 provides the method of example 11, where the heart measurement is heart rate variability (HRV), the method further including determining whether a driver in the vehicle seat is experiencing a health issue at least in part based on the HRV; and generating an alert in response to determining that the driver is experiencing a health issue.

Example 14 provides the method of example 11, where filtering the target signal includes applying a recursive least squares (RLS) filter to the target signal.

Example 15 provides the method of example 11, where the first sensor is one of an array of sensors at different positions along the left side of the backrest, the method further including selecting the first sensor from the array of sensors based on the first sensor providing the strongest heart signal of the array of sensors.

Example 16 provides the method of example 11, where the first sensor is a first acoustic sensor, and the second sensor is a second acoustic sensor.

Example 17 provides the method of example 11, where the first sensor is a first piezoelectric sensor, and the second sensor is a second piezoelectric sensor.

Example 18 provides a non-transitory computer-readable media having instructions stored thereon, where the instructions, when executed by a device, cause the device to obtain a target signal from a first sensor positioned in a backrest of a vehicle seat, the first sensor positioned along a left side of the backrest to capture a heart sounds and noise; obtain a reference signal from a second sensor positioned in the backrest of the vehicle seat, the second sensor positioned along a right side of the backrest; filter the target signal using the reference signal to generate a filtered signal, where filtering the target signal removes at least a portion of the noise from the target signal; and determine a heart measurement based on the filtered signal.

Example 19 provides the non-transitory computer-readable media of example 18, where the heart measurement is a heart rate, and the instructions further cause the device to compare the heart rate to at least one threshold to determine whether a driver in the vehicle seat is experiencing a health issue; and generate an alert in response to determining that the driver is experiencing a health issue.

Example 20 provides the non-transitory computer-readable media of example 18, where filtering the target signal includes applying a recursive least squares (RLS) filter to the target signal.

OTHER IMPLEMENTATION NOTES, VARIATIONS, AND APPLICATIONS

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

In one example embodiment, any number of electrical circuits of the figures may be implemented on a board of an associated electronic device. The board can be a general circuit board that can hold various components of the internal electronic system of the electronic device and, further, provide connectors for other peripherals. More specifically, the board can provide the electrical connections by which the other components of the system can communicate electrically. Any suitable processors (inclusive of digital signal processors, microprocessors, supporting chipsets, etc.), computer-readable non-transitory memory elements, etc. can be suitably coupled to the board based on particular configuration needs, processing demands, computer designs, etc. Other components such as external storage, additional sensors, controllers for audio/video display, and peripheral devices may be attached to the board as plug-in cards, via cables, or integrated into the board itself. In various embodiments, the functionalities described herein may be implemented in emulation form as software or firmware running within one or more configurable (e.g., programmable) elements arranged in a structure that supports these functions. The software or firmware providing the emulation may be provided on non-transitory computer-readable storage medium comprising instructions to allow a processor to carry out those functionalities.

It is also imperative to note that all of the specifications, dimensions, and relationships outlined herein (e.g., the number of processors, logic operations, etc.) have only been offered for purposes of example and teaching only. Such information may be varied considerably without departing from the spirit of the present disclosure, or the scope of the appended claims. The specifications apply only to one non-limiting example and, accordingly, they should be construed as such. In the foregoing description, example embodiments have been described with reference to particular arrangements of components. Various modifications and changes may be made to such embodiments without departing from the scope of the appended claims. The description and drawings are, accordingly, to be regarded in an illustrative rather than in a restrictive sense.

Note that with the numerous examples provided herein, interaction may be described in terms of two, three, four, or more components. However, this has been done for purposes of clarity and example only. It should be appreciated that the system can be consolidated in any suitable manner. Along similar design alternatives, any of the illustrated components, modules, and elements of the FIGS. may be combined in various possible configurations, all of which are clearly within the broad scope of this Specification.

Note that in this Specification, references to various features (e.g., elements, structures, modules, components, steps, operations, characteristics, etc.) included in "one embodiment", "example embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. Note that all optional features of the systems and methods described above may also be implemented with respect to the methods or systems described herein and specifics in the examples may be used anywhere in one or more embodiments.

In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke paragraph (f) of 35 U.S.C. Section 112 as it exists on the date of the filing hereof unless the words "means for" or "step for" are specifically used in the particular claims; and (b) does not intend, by any statement in the Specification, to limit this disclosure in any way that is not otherwise reflected in the appended claims.

What is claimed is:

1. A system, comprising:
 a first sensor positioned in a backrest of a vehicle seat, the first sensor positioned along a first side of the backrest to capture a target signal representative of heart sounds and noise;
 a second sensor positioned in the backrest of the vehicle seat, the second sensor positioned along a second side of the backrest to capture a reference signal that represents, at least partially, second noise and is devoid of non-attenuated heart sounds relative to the heart sounds, with the second side being opposite the first side relative to a center line of the backrest; and
 processing circuitry configured to:
  receive the target signal;
  receive the reference signal;
  filter the target signal using the reference signal to generate a filtered signal, wherein filtering the target signal removes at least a portion of the noise from the target signal; and
  determine a heart measurement based on the filtered signal.

2. The system of claim 1, wherein the heart measurement is a heart rate, and the processing circuitry is further configured to compare the heart rate to at least one threshold value to determine whether a driver in the vehicle seat is experiencing a health issue that impairs the driver's ability to drive.

3. The system of claim 1, wherein the heart measurement is heart rate variability (HRV), and the processing circuitry is further configured to determine, based at least in part based on the HRV, whether a driver in the vehicle seat is experiencing a health issue that impairs the driver's ability to drive.

4. The system of claim 1, wherein the filtering the target signal comprises performing an adaptive filtering algorithm.

5. The system of claim 4, wherein the adaptive filtering algorithm comprises a recursive least squares (RLS) filter.

6. The system of claim 1, wherein the first sensor is one of an array of sensors at different positions along the first side of the backrest.

7. The system of claim 6, wherein the processing circuitry is further configured to select the first sensor from the array of sensors, the first sensor providing the strongest heart signal of heart signals from the array of sensors.

8. The system of claim 6, wherein the processing circuitry is further configured to:
 generate a plurality of filtered signals using the reference signal, wherein a first filtered signal of the plurality of filtered signals corresponds to a first target signal from the array of sensors, and wherein a second filtered signal of the plurality of filtered signals corresponds to a second target signal from the array of sensors; and
 determine the heart measurement based on the plurality of filtered signals.

9. The system of claim 1, wherein the first sensor is a first acoustic sensor, and the second sensor is a second acoustic sensor.

10. The system of claim 1, wherein the first sensor is a first piezoelectric sensor, and the second sensor is a second piezoelectric sensor.

11. A method, comprising:
 obtaining a target signal from a first sensor positioned in a backrest of a vehicle seat, the first sensor positioned along a first side of the backrest to capture heart sounds and noise;
 obtaining a reference signal from a second sensor positioned in the backrest of the vehicle seat, the second sensor positioned along a second side of the backrest, with the second side opposite the first side relative to a center line of the backrest, wherein the reference signal is representative, at least partially, of second noise and is devoid of non-attenuated heart sounds relative to the heart sounds;
 filtering, by processing circuitry, the target signal using the reference signal to generate a filtered signal, wherein filtering the target signal removes at least a portion of the noise from the target signal; and
 determining, by the processing circuitry, a heart measurement based on the filtered signal.

12. The method of claim 11, wherein the heart measurement is a heart rate, the method further comprising:
 comparing the heart rate to at least one threshold value to determine that a driver in the vehicle seat is experiencing a health issue that impairs the driver's ability to drive; and generating an alert in response to determining that the driver is experiencing the health issue.

13. The method of claim 11, wherein the heart measurement is heart rate variability (HRV), the method further comprising:
   determining based at least in part based on the HRV, that a driver in the vehicle seat is experiencing a health issue that impairs the driver's ability to drive; and
   generating an alert in response to determining that the driver is experiencing the health issue.

14. The method of claim 11, wherein the filtering the target signal comprises applying a recursive least squares (RLS) filter to the target signal.

15. The method of claim 11, wherein the first sensor is one of an array of sensors at different positions along the first side of the backrest, the method further comprising selecting the first sensor from the array of sensors based on the first sensor providing the strongest heart signal of heart signals from the array of sensors.

16. The method of claim 11, wherein the first sensor is a first acoustic sensor, and the second sensor is a second acoustic sensor.

17. The method of claim 11, wherein the first sensor is a first piezoelectric sensor, and the second sensor is a second piezoelectric sensor.

18. A non-transitory computer-readable media having instructions stored thereon, wherein the instructions, when executed by a device, cause the device to:
   obtain a target signal from a first sensor positioned in a backrest of a vehicle seat, the first sensor positioned along a first side of the backrest to capture heart sounds and noise;
   obtain a reference signal from a second sensor positioned in the backrest of the vehicle seat, the second sensor positioned along a second side of the backrest, with the second side being opposite the first side relative to a center line of the backrest, wherein the reference signal is representative, at least partially, of second noise and is devoid of non-attenuated heart sounds relative to the heart sounds;
   filter the target signal using the reference signal to generate a filtered signal, wherein filtering the target signal removes at least a portion of the noise from the target signal; and
   determine a heart measurement based on the filtered signal.

19. The non-transitory computer-readable media of claim 18, wherein the heart measurement is a heart rate, and the instructions, when executed by the device, further cause the device to:
   compare the heart rate to at least one threshold value to determine that a driver in the vehicle seat is experiencing a health issue that impairs the driver's ability to drive; and
   generate an alert in response to determining that the driver is experiencing the health issue.

20. The non-transitory computer-readable media of claim 18, wherein filtering the target signal comprises applying a recursive least squares (RLS) filter to the target signal.

* * * * *